(12) United States Patent
Gerlach et al.

(10) Patent No.: US 7,211,588 B2
(45) Date of Patent: May 1, 2007

(54) N-SUBSTITUTED INDOLYL-3-GLYOXYLAMIDES, THEIR USE AS MEDICAMENTS AND PROCESS FOR THEIR PREPARATION

(75) Inventors: Matthias Gerlach, Brachttal (DE); Tilmann Schuster, Frankfurt (DE); Peter Schmidt, Schöneck (DE); Silke Baasner, Schöneck (DE); Eckhard Günther, Maintal (DE)

(73) Assignee: Zentaris GmbH, Frankfurt (DE)

( * ) Notice: Subject to any disclaimer, the term of this patent is extended or adjusted under 35 U.S.C. 154(b) by 117 days.

(21) Appl. No.: 10/892,040

(22) Filed: Jul. 15, 2004

(65) Prior Publication Data

US 2005/0020636 A1    Jan. 27, 2005

Related U.S. Application Data

(60) Provisional application No. 60/490,004, filed on Jul. 25, 2003.

(51) Int. Cl.
*A61K 31/4709* (2006.01)
*C07D 215/38* (2006.01)

(52) U.S. Cl. .................................. 514/314; 546/159
(58) Field of Classification Search ............ 514/314; 546/159
See application file for complete search history.

(56) References Cited

U.S. PATENT DOCUMENTS

| 6,232,327 | B1 | 5/2001 | Nickel et al. |
|---|---|---|---|
| 6,251,923 | B1 | 6/2001 | Hofgen et al. |
| 6,432,987 | B2 | 8/2002 | Gunther et al. |
| 6,693,119 | B2 | 2/2004 | Nickel et al. |
| 2003/0092751 | A1 | 5/2003 | Koya et al. |
| 2003/0100597 | A1 | 5/2003 | Emig et al. |

2004/0029858 A1    2/2004  Menta et al.

FOREIGN PATENT DOCUMENTS

| WO | WO 00/67802 | 11/2000 |
|---|---|---|
| WO | WO 01/47913 | 7/2001 |
| WO | WO 01/58893 A2 | 8/2001 |
| WO | WO 02/08225 AZ | 1/2002 |
| WO | WO 03/022280 A2 | 3/2003 |

OTHER PUBLICATIONS

Freshney (Culture of Animal Cells, A Manual of Basic Technique, Alan R. Liss, Inc., 1983, New York, p. 4).*
Dermer (Biocechnology, 1994, 12:320).*
Bacher, et al., "D-24851, A Novel Synthetic Microtubule Inhibitor, Exerts Curative Antitumoral Activity in Vivo, Shows Efficacy toward Multidrug-resistant Tumor Cells, and Lacks Neurotoxicity", Cancer Research 61(1), pp. 392-399, Jan. 1, 2001.*
Wen-Tai Li et al.,Synthesis and Biological Evaluation of N-Heterocyclic Indolyl Glyoxylamides as Orally Active Anticancer Agents, J. Med. Chem 2003, 46, 1706-1715.

* cited by examiner

*Primary Examiner*—Joseph K. McKane
(74) *Attorney, Agent, or Firm*—Goodwin Procter LLP

(57) ABSTRACT

The invention relates to novel N-substituted indolyl-3-glyoxylamides of the general formula I, their preparation and use as medicaments, in particular for the treatment of tumors

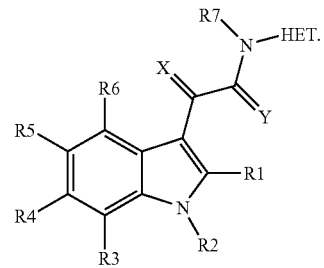

12 Claims, No Drawings

N-SUBSTITUTED INDOLYL-3-GLYOXYLAMIDES, THEIR USE AS MEDICAMENTS AND PROCESS FOR THEIR PREPARATION

CROSS-REFERENCE TO RELATED APPLICATION

This application claims the benefit of priority to U.S. Provisional Application No. 60/490,004 filed on Jul. 25, 2003, which is incorporated herein by reference in its entirety.

BACKGROUND OF THE INVENTION

For the next few years, a dramatic increase in oncoses and tumor-related cases of death is expected worldwide. In 2001, worldwide approximately 10 million people were suffering from cancer and over 6 million people died from this disease. The development of tumors is a fundamental disease of higher organisms in flora and fauna. The generally recognized multistep model of carcinogenesis assumes that as a result of accumulation of a number of mutations in an individual cell this is so modified in its proliferation and differentiation behavior that finally, via benign intermediate stages, a malignant, state with metastasis is reached. Behind the term cancer or tumor, a clinical picture with more than 200 various individual diseases hides itself. Oncoses can proceed in a benign or malignant manner. The most important tumors are those of the lung, the breast, the stomach, the neck of the uterus, the prostate, the head and neck, the large and small intestine, the liver and the blood system. There are great differences with respect to course, prognosis and therapy behavior. More than the 90% of the cases recognized relate to solid tumors, which in particular in the advanced stage or on metastasis are treatable with difficulty or untreatable. The three pillars of cancer control are still surgical removal, irradiation and chemotherapy. In spite of great advances it has still not been possible to develop medicaments which bring about a marked prolongation of the survival time or even a complete cure in the widespread solid tumors.

It is therefore meaningful to invent novel medicaments for the control of cancer. In particular, the disadvantageous formation of resistance, as is known of many antitumor agents, should be circumvented.

Indolyl-3-glyoxylamides are frequently used as pharmacologically active compounds and as synthesis components in pharmaceutical chemistry.

In WO03/022280, N-substituted alkyl- and aryl-3-glyoxylamide indoles having antitumoral action are described. Actual exemplary embodiments of this substitution pattern on the glyoxylamide nitrogen atom are, however, not given.

In the documents WO99/51224 A1 and WO01/22954 A1, N-substituted indol-3-yl derivatives having antitumor action are described. Actual exemplary embodiments of this substitution pattern are, however, not given.

In WO99/55696 A1, substituted hydroxyindoles are described as phosphodiesterase 4 inhibitors. An antitumoral activity of the compounds according to the invention is neither described nor suggested.

In WO 02/08225 A1, 2-(1H-indol-3-yl)-2-oxoacetamide derivatives having antitumor action against solid tumors are described. However, the invention does not relate to actual exemplary embodiments with substitution on the glyoxylamide nitrogen atom.

In patent specification WO 00/67802, indole-3-glyoxylamides which are substituted by higher chain fatty acids are described as potential antitumor agents. Actual exemplary embodiments are, however, not given or confirmed by biological data.

In the publication of W.-T. Li et al. (J. Med. Chem. 2003, 46, 1706 ff.), N-heterocyclic indolylglyoxylamides are described as orally active compounds having antitumoral activity.

WO02/10152 A2 of the applicant already describes another class of indole derivatives for the treatment of tumors. Inter alia, the active compound N-(2-methyl-6-quinolyl)-[1-(4-chlorobenzyl)-indol-3-yl]glyoxylamide was tested here on various tumor cell lines for its antiproliferative action.

SUMMARY OF THE INVENTION

The present invention relates to novel N-substituted indolyl-3-glyoxylamides, their preparation and use as medicaments for the treatment of benign and malignant tumors in mammals, including humans.

DETAILED DESCRIPTION OF THE INVENTION

In the present application, N-substituted indolyl-3-glyoxylamides as in the general formula I

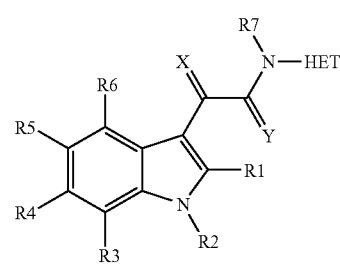

are described, in which
R1, R3–R6:
  are hydrogen,
  unsubstituted or substituted alkyl,
  unsubstituted or substituted cycloalkyl,
  unsubstituted or substituted aryl,
  unsubstituted or substituted heteroaryl,
  unsubstituted or substituted alkylaryl,
  unsubstituted or substituted alkylheteroaryl,
  amino, monoalkylamino, dialkylamino,
  halogen, alkyl substituted by one or more fluorine atoms, preferably a trifluoromethyl group,
cyano, straight-chain or branched cyanoalkyl,
alkylcarbonyl,
carboxyl, alkoxycarbonyl, carboxyalkyl or alkoxycarbonylalkyl,
alkoxy,
arylalkoxy, preferably benzyloxy,
alkoxycarbonylamino, alkoxycarbonylaminoalkyl, R2:
is unsubstituted or substituted alkyl,
unsubstituted or substituted alkylaryl,
unsubstituted or substituted alkylheteroaryl, R7: is a sulfone of the formula —SO2-X1, where X1 is N(alk)$_2$, hydroxyl, unsubstituted or substituted alkyl, unsubstituted or substituted cycloalkyl, unsubstituted or substituted aryl, unsubstituted or substituted heteroaryl, unsubstituted or substituted alkylcycloalkyl, unsubstituted or substituted alkylheterocyclyl, unsubstituted or substituted alkylaryl, unsubstituted or substituted alkylheteroaryl;

C(O)—X2, where X2 is unsubstituted or substituted aryl, unsubstituted or substituted heteroaryl, unsubstituted or substituted alkylaryl and unsubstituted or substituted alkylheteroaryl, C(O)O—X3, where X3 is unsubstituted or substituted cycloalkyl, unsubstituted or substituted heterocyclyl, unsubstituted or substituted aryl, unsubstituted or substituted heteroaryl, unsubstituted or substituted alkylcycloalkyl, unsubstituted or substituted alkylheterocyclyl, and unsubstituted or substituted alkylheteroaryl, C(O)NX4X5, where X4 and X5 independently of one another are hydrogen, unsubstituted or substituted alkyl, unsubstituted or substituted cycloalkyl, unsubstituted or substituted heterocyclyl, unsubstituted or substituted aryl, unsubstituted or substituted heteroaryl, unsubstituted or substituted alkylcycloalkyl, unsubstituted or substituted alkylheterocyclyl, unsubstituted or substituted alkylaryl, unsubstituted or substituted alkylheteroaryl, or X4 and X5 together are cycloalkyl or cycloheteroalkyl, C(S)NX6X7, where X6 and X7 independently of one another are hydrogen, unsubstituted or substituted alkyl, unsubstituted or substituted cycloalkyl, unsubstituted or substituted heterocyclyl, unsubstituted or substituted aryl, unsubstituted or substituted heteroaryl, unsubstituted or substituted alkylcycloalkyl, unsubstituted or substituted alkylheterocyclyl, unsubstituted or substituted alkylaryl, unsubstituted or substituted alkylheteroaryl, or X6 and X7 together are cycloalkyl or cycloheteroalkyl, X: is O, S or geminally linked hydrogen and hydroxyl,
Y: is O or S
and
HET: is a saturated, unsaturated or aromatic (C2–C14)-heterocycle comprising one or more heteroatoms selected from the group consising of N, O and S, which can be bonded to the amide nitrogen directly or via a (C1–C6)-alkyl bridge and the alkyl radical can be substituted or unsubstituted and optionally one or two aryl or cycloalkyl groups can be fused to the heterocycle, and
the heterocyclyl, aryl or cycloalkyl groups can be unsubstituted or substituted and the alkyl radical can in all cases be branched or unbranched and saturated or unsaturated,
and their pharmaceutically tolerable salts.

The substituent HET can in particular be pyrrole, furan, thiophene, pyrazole, thiazole, indole, oxazole, imidazole, isothiazole, isoxazole, 1,2,3-triazole, 1,2,4-triazole, 1,2,4-oxadiazole, 1,3,4-oxadiazole, 1,2,5-thiadiazole, 1,3,4-thiadiazole, tetrazole, pyridine, pyrimidine, pyridazine, pyrazine, benzofuran, indazole, carbazole, benzoxazole, benzimidazole, benzothiazole, benzotriazole, quinoline, isoquinoline, cinnoline, quinoxaline, quinazoline, phthalazine, pyridopyrazine, 1,2,3-triazine, 1,2,4-triazine, 1,3,5-triazine, purine, pteridine, acridine and phenanthridine.

The expression "alkyl" within the meaning of this invention comprises acyclic saturated or unsaturated hydrocarbons having 1 to 20 C atoms, which can be branched or straight-chain and unsubstituted or mono- or polysubstituted.

The expression "cycloalkyl" denotes cyclic hydrocarbons having 3–12 carbon atoms, which can be saturated or unsaturated, unsubstituted or mono- or poly-substituted.

The expression "aryl" denotes aromatic hydrocarbons having 6–14 C atoms, which can be unsubstituted or mono- or polysubstituted, where the aryl substituents are identical or different and can be present in any desired and possible position of the aryl.

The expression "heteroaryl" stands for a 5-, 6- or 7-membered cyclic aromatic radical, which contains at least 1, optionally also 2, 3, 4 or 5 heteroatoms, where the heteroatoms are identical or different and the heterocycle can be unsubstituted or mono- or polysubstituted. In the case of the substitution on the heteroaryl moiety the heteroaryl substituents can be identical or different and can be in any desired and possible position of the heteroaryl. Preferred heteroatoms are nitrogen, oxygen and sulfur.

The expression "heterocyclyl" stands for a 3-, 4-, 5-, 6-, 7- or 8-membered cyclic organic radical, which contains at least 1, optionally 2, 3, 4 or 5 heteroatoms, where the heteroatoms are identical or different and the cyclic radical is saturated or unsaturated, but not aromatic and can be unsubstituted or mono- or polysubstituted. Preferred heteroatoms are nitrogen, oxygen and sulfur.

The expressions "alkylcycloalkyl", "alkylheterocyclyl", "alkylaryl or "alkylheteroaryl" mean that alkyl and cycloalkyl, heterocyclyl, aryl and heteroaryl have the meanings mentioned and the cycloalkyl, heterocyclyl, aryl or heteroaryl radical is bonded to the compound of the general formula I via a C1–C8-alkyl group.

In connection with "alkyl", the term substituted is to be understood within the meaning of this invention as meaning the substitution of a hydrogen radical by F, Cl, Br, I, CN, NH$_2$, NH-alkyl, NH-cycloalkyl, NH-aryl, NH-heteroaryl, NH-alkylaryl, NH-alkylheteroaryl, NH-heterocyclyl, NH-alkyl-OH, N(alkyl)$_2$, N(alkylaryl)$_2$, N(alkylheteroaryl)$_2$, N(heterocyclyl)$_2$, N(alkyl-OH)$_2$, NO, NO$_2$, SH, S-alkyl, S-cycloalkyl, S-aryl, S-heteroaryl, S-alkylaryl, S-alkylheteroaryl, S-heterocyclyl, S-alkyl-OH, S-alkyl-SH, S-alkyl, S—S-cycloalkyl, S—S-aryl, S—S-heteroaryl, S—S-alkylaryl, S—S-alkylheteroaryl, S—S-heterocyclyl, S—S-alkyl-OH, S—S-alkyl-SH, S—S-alkyl-C(O)—NH-heterocyclyl, OH, O-alkyl, O-cycloalkyl, O-aryl, O-heteroaryl, O-alkylaryl, O-alkylheteroaryl, O-heterocyclyl, O-alkyl-OH, CHO, C(O)-alkyl, C(S)-alkyl, C(O)-aryl, C(S)-aryl, C(O)-alkylaryl, C(S)-alkylaryl, C(O)-heterocyclyl, C(O)-heteroaryl, C(O)-alkylheteroaryl, C(S)-heterocyclyl, CO$_2$H, CO$_2$-alkyl, CO$_2$-cyclyl, CO$_2$-heterocyclyl, CO$_2$-aryl, CO$_2$-heteroaryl, CO$_2$-alkylaryl, C(O)—NH$_2$, C(O)NH-alkyl, C(O)NH-aryl, C(O)NH-heterocyclyl, C(O)NH-alkylheterocyclyl, C(O)N(alkyl)$_2$, C(O)N(alkylaryl)$_2$, C(O)N(alkylheteroaryl)$_2$, C(O)N(heterocyclyl)$_2$, SO-alkyl, SO$_2$-alkyl, SO$_2$NH$_2$, SO$_3$H, alkyl, cycloalkyl, aryl, heteroaryl, or heterocyclyl, where polysubstituted radicals are to be understood as meaning those which are either polysubstituted, e.g. di- or trisubstituted, on different or on identical atoms, for example trisubstituted on the same C atom as in the case of CF$_3$, —CH$_2$CF$_3$ or in different positions as in the case of —CH(OH)—CH=CH—CHCl$_2$. Polysubstitution can take place with the same or different substituents.

With respect to aryl, heterocyclyl, heteroaryl, alkylaryl and cycloalkyl, mono- or polysubstituted is understood within the meaning of this invention as meaning the mono- or polysubstitution, e.g. di-, tri- or tetrasubstitution, of one or more hydrogen atoms of the ring system by F, Cl, Br, I, CN, NH$_2$, NH-alkyl, NH-aryl, NH-heteroaryl, NH-alkylaryl, NH-alkylheteroaryl, NH-heterocyclyl, NH-alkyl-OH, N(alkyl)$_2$, NC(O)alkyl, N(alkylaryl)$_2$, N(alkylheteroaryl)$_2$, N(heterocyclyl)$_2$, N(alkyl-OH)$_2$, NO, NO$_2$, SH, S-alkyl, S-aryl, S-heteroaryl, S-alkylaryl, S-alkylheteroaryl, S-heterocyclyl, S-alkyl-OH, S-alkyl-SH, OH, O-alkyl, O-aryl, O-heteroaryl, O-alkylaryl, O-alkylheteroaryl, O-heterocyclyl, O-alkyl-OH, O—C(O)-alkyl, CHO, C(O)-alkyl, C(S)-alkyl, C(O)-aryl, C(S)-aryl, C(O)-alkylaryl, C(S)-alkylaryl, C(O)-heterocyclyl, C(S)-heterocyclyl, CO$_2$H, CO$_2$-alkyl, CO$_2$-alkylaryl, C(O)—NH$_2$, C(O)NH-alkyl, C(O)NH-aryl, C(O)NH-heterocyclyl, C(O)N(alkyl)$_2$, C(O)N(alkylaryl)$_2$, C(O)N(alkylheteroaryl)$_2$, C(O)N(heterocyclyl)$_2$, SO-alkyl, SO$_2$-alkyl, SO$_2$-aryl, SO$_2$-heteroaryl, SO$_2$NH$_2$, SO$_3$H, CF$_3$, CHO, CHS, alkyl, cycloalkyl, aryl, heteroaryl, and/or heterocyclyl, on one or optionally different atoms (where one substituent can optionally for its part be substituted). Polysubstitution in this case takes place with the same or with different substituents.

If the compounds of the general formula I according to the invention have at least one asymmetric center, they can be present in the form of their racemates, in the form of the pure enantiomers and/or diastereomers or in form of mixtures of these enantiomers and/or diastereomers, namely both in substance and as pharmaceutically acceptable salts of these compounds. The mixtures can be present in any desired mixing ratio of the stereoisomers.

If possible, the compounds according to the invention can be present in the form of the tautomers.

The compounds of the general formula I according to the invention can be converted, if they have a sufficiently basic group, such as, for example, a secondary or tertiary amine, into salts with inorganic and organic acids. Preferably, the pharmaceutically acceptable salts of the compounds according to the invention as in the general formula I are formed with hydrochloric acid, hydrobromic acid, sulfuric acid, phosphoric acid, methanesulfonic acid, p-toluenesulfonic acid, carbonic acid, formic acid, acetic acid, trifluoroacetic acid, oxalic acid, malonic acid, maleic acid, succinic acid, tartaric acid, racemic acid, malic acid, embonic acid, mandelic acid, fumaric acid, lactic acid, citric acid, glutamic acid or aspartic acid. The salts formed are, inter alia, hydrochlorides, hydrobromides, sulfates, phosphates, methanesulfonates, sulfoacetates, tosylates, carbonates, hydrogencarbonates, formates, acetates, triflates, oxalates, malonates, maleates, succinates, tartrates, malates, embonates, mandelates, fumarates, lactates, citrates and glutamates. The stoichiometry of the salts of the compounds according to the invention formed can in this case be integral or nonintegral multiples of 1.

The compounds of the general formula I according to the invention can, if they contain a sufficiently acidic group, such as, for example, the carboxyl group, be converted into their physiologically tolerable salts with inorganic and organic bases. Possible inorganic bases are, for example, sodium hydroxide, potassium hydroxide, calcium hydroxide, organic bases are ethanolamine, diethanolamine, triethanolamine, cyclohexylamine, dibenzylethylenediamine and lysine. The stoichiometry of the salts of the compounds according to the invention formed can in this case be integral or nonintegral multiples of 1.

Likewise preferred are solvates and in particular hydrates of the compounds according to the invention, which can be obtained, for example, by crystallization from a solvent or from aqueous solution. It is possible here to combine one, two, three or as many solvate or water molecules as desired with the compounds according to the invention to give solvates and hydrates.

Most preference is given to compounds as per the general formula I which have been included in the following selection:

N-{2-[1-(4-chlorobenzyl)-1H-indol-3-yl]-2-oxoacetyl}-N-quinolin-6-yl-benzamide (1)

N-{2-[1-(4-chlorobenzyl)-1H-indol-3-yl]-2-oxoacetyl}-2-phenyl-N-quinolin-6-yl-acetamide (2)

phenyl{2-[1-(4-chlorobenzyl)-1H-indol-3-yl]-2-oxoacetyl}quinolin-6-ylcarbamate (3)

(1R,2S,5R)-2-isopropyl-5-methylcyclohexyl{2-1-(4-chlorobenzyl)-1H-indol-3-yl]-2-oxoacetyl}quinolin-6-ylcarbamate (4)

N-{2-[1-(4-chlorobenzyl)-1H-indol-3-yl]-2-oxoacetyl}-4-methyl-N-quinolin-6-yl-benzenesulfonamide (5)

The present invention's indolyl-3-glyoxylamides as per the general formula I are useful for treating mammals, including humans. Mammals other than humans can be domestic animals such as horses, cows, dogs, cats, hares, sheep and the like.

A further aspect of the invention is a process for the treatment of tumors in a mammal, including a human being, which comprises administering at least one indolyl-3-glyoxylamide of the general formula I to the mammal in a dose which is efficacious for tumor treatment. The therapeutically effective dose to be administered for the treatment of the respective indolyl-3-glyoxylamide according to the invention depends, inter alia, on the nature and the stage of the tumor disease, the age and sex of the patient, the manner of administration and the duration of the treatment. The medicaments according to the invention can be administered as liquid, semisolid and solid pharmaceutical forms. This is carried out in the manner suitable in each case in the form of aerosols, powders and dusting powders, tablets, coated tablets, emulsions, foams, solutions, suspensions, gels, ointments, pastes, pills, pastilles, capsules or suppositories.

The pharmaceutical forms, in addition to at least one constituent according to the invention, contain, depending on the pharmaceutical form employed, excipients where appropriate, such as, inter alia, solvents, solution accelerants, solubilizers, emulsifiers, wetting agents, antifoams, gel-formers, thickeners, film-formers, binders, buffers, salt-formers, driers, flow regulators, fillers, preservatives, antioxidants, colorants, mold release agents, lubricants, disintegrants, taste and odor coregents. The selection of the excipients and also the amounts which are to be used thereof depends on the pharmaceutical form chosen and is guided by the formulations known to one skilled in the art.

The medicaments according to the invention can be administered in a suitable administration form to the skin, epicutaneously as a solution, suspension, emulsion, foam, ointment, paste or patch; via the oral and buccal mucosa, buccally, lingually or sublingually as a tablet, pastille, coated tablets, linctus or gargle; via the gastric and intestinal mucosa, enterally as a tablet, coated tablets, capsule, solution, suspension or emulsion; via the rectal mucosa, rectally as a suppository, rectal capsule or ointment; via the nasal mucosa, nasally as drops, ointments or spray; via the bronchial and alveolar epithelium, pulmonarily or by inhalation as an aerosol or inhalant; via the conjunctiva, conjunctivally as eyedrops, eye ointment, eye tablets, lamellae or eye lotion; via the mucosae of the genital organs, intravaginally as vaginal suppositories, ointments and flush, intrauterinely as uterine pessaries; via the efferent ureters, intraurethrally as a flush, ointment or medicated probe; into an artery, intraarterially as an injection; into a vein, intravenously as an injection or infusion, parverously as an injection or infusion; into the skin, intracutaneously as an injection or implant; under the skin, subcutaneously as an injection or implant; into the muscle, intramuscularly as an injection or implant; into the abdominal cavity, intraperitoneally as an injection or infusion.

The compounds of the general structure I according to the invention can be retarded in their pharmaceutical action with respect to practical therapeutic requirements by means of suitable measures. This aim can be achieved in a chemical and/or pharmaceutical way. Examples of the achievement of a prolongation of action are the use of implants, liposomes, sustained release forms, nanoparticle suspensions and "prodrugs" of the compounds according to the invention, the formation of poorly soluble salts and complexes or the use of crystal suspensions.

The compounds according to the invention can be employed as an individual substance or in combination with further cytotoxic substances, such as, for example, cisplatin, carboplatin, doxorubicin, ifosfamide, cyclophosphamide, 5-FU, methotrexate and in particular in combination with inhibitors of signal transduction, such as, for example, Herceptin, Glivec or Iressa.

Particular preference is given to medicaments which comprise at least one compound from the following group of indolyl-3-glyoxyl derivatives:

N-{2-[1-(4-chlorobenzyl)-1H-indol-3-yl]-2-oxoacetyl}-N-quinolin-6-yl-benzamide (1)

N-{2-[1-(4-chlorobenzyl)-1H-indol-3-yl]-2-oxoacetyl}-2-phenyl-N-quinolin-6-yl-acetamide (2)

phenyl{2-[1-(4-chlorobenzyl)-1H-indol-3-yl]-2-oxoacetyl}quinolin-6-ylcarbamate (3)

(1R,2S,5R)-2-isopropyl-5-methylcyclohexyl{2-1-(4-chlorobenzyl)-1H-indol-3-yl]-2-oxoacetyl}quinolin-6-ylcarbamate (4)

N-{2-[1-(4-chlorobenzyl)-1H-indol-3-yl]-2-oxoacetyl}-4-methyl-N-quinolin-6-yl-benzenesulfonamide (5)

These compounds can be present not only as a free base but also as salts of physiologically tolerable acids.

The invention additionally comprises processes for the preparation of the compounds of the structure I according to the invention.

The compounds (I) according to the invention can be synthesized as in scheme 1 below:

Scheme 1

Stage 1
1) base, R2-Hal
   aprotic solvent
2) (COCl)2
3) HET—NH2,
   base aprotic solvent

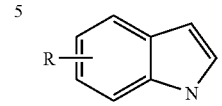

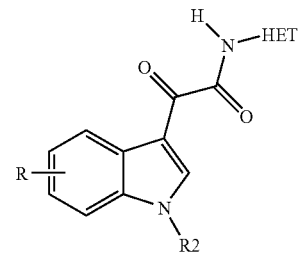

Stage 2
"R7", base
aprotic solvent

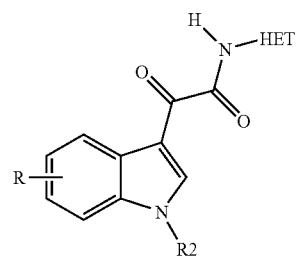

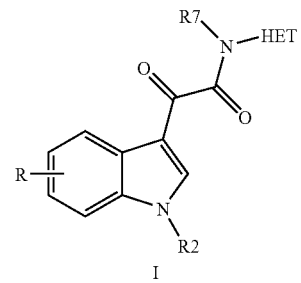

I

According to this general procedure for stages 1 and 2, on which synthesis scheme 1 is based, the following compounds were synthesized which follow from the list below with statement of the respective chemical name. The analytical characterization of the compounds according to the invention was carried out by means of their melting points or by $^1$H-NMR spectroscopy and/or mass spectrometry.

The chemicals and solvents employed were obtained commercially from the conventional suppliers (Acros, Avocado, Aldrich, Fluka, Lancaster, Maybridge, Merck, Sigma, TCI etc.) or synthesized.

The invention will now be illustrated in more detail with the aid of the examples below, without being limited thereto.

The present invention's compounds 1–5 were synthesized as per the following General Prescription:

To a mixture of 1.2 mmol of sodium hydride (60% mineral oil suspension) in 50 ml of dimethylformamide or THF are added 1.2 mmol of 2-[1-(4-chlorobenzyl)-1H-indol-3-yl]-2-oxo-N-quinolin-6-ylacetamide with ice cooling. After 15 min of stirring at room temperature, 1.3 mmol of the corresponding acyl chloride are added and the ice cooling is removed. After 3 h, the reaction solution is poured onto ice-water and extracted three times with 100 ml of ethyl acetate each time. The combined organic phases are dried over sodium sulfate and concentrated to dryness. The crude product thus obtained is subsequently purified by recrystallization or by column chromatography.

EXAMPLE 1
N-{2-[1-(4-Chlorobenzyl)-1H-indol-3-yl]-2-oxoacetyl}-N-quinolin-6-ylbenzamide (1)

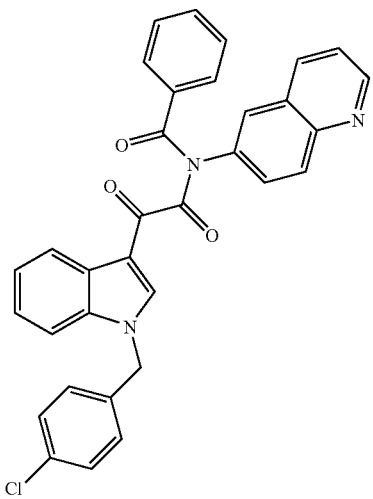

Melting point: 213° C.
$^1$H-NMR (DMSO-d$_6$) δ=8.94–8.95 (m, 2H), 8.70 (s, 1H), 8.35 (d, 1H), 8.08–8.09 (m, 2H), 8.03 (d, 1H), 7.85 (dd, 1H), 7.73 (d, 2H), 7.62 (d, 1H), 7.55–7.58 (m, 1H), 7.41–7.46 (m, 3H), 7.27–7.36 (m, 6H), 5.60 (s, 2H) ppm.

EXAMPLE 2
N-{2-[1-(4-Chlorobenzyl)-1H-indol-3-yl]-2-oxoacetyl}-2-phenyl-N-quinolin-6-ylacetamide (2)

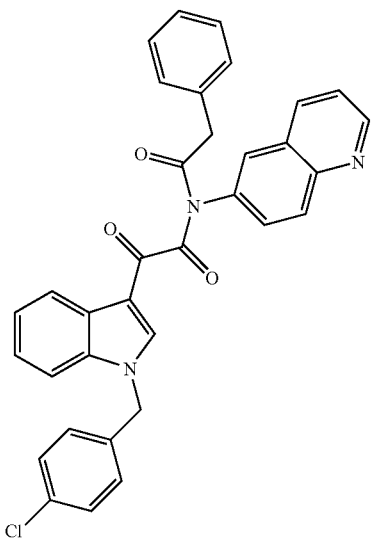

MS: m/e=558.0 (M+H$^+$)

EXAMPLE 3
Phenyl{2-[1-(4-chlorobenzyl)-1H-indol-3-yl]-2-oxoacetyl}quinolin-6-ylcarbamate (3)

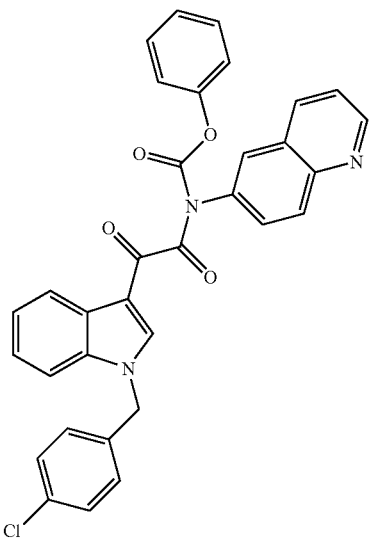

MS: m/e=560.0 (M+H$^+$)

EXAMPLE 4
(1R,2S,5R)-2-Isopropyl-5-methylcyclohexyl{2-[1-(4-chlorobenzyl)-1H-indol-3-yl]-2-oxoacetyl}quinolin-6-ylcarbamate (4)

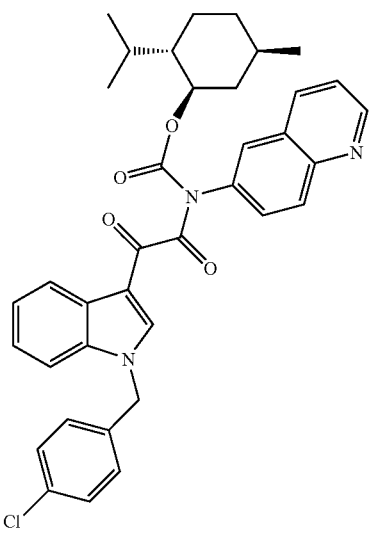

MS: m/e=622.0 (M+H$^+$)

EXAMPLE 5

N-{2-[1-(4-Chlorobenzyl)-1H-indol-3-yl]-2-oxoacetyl}-4-methyl-N-quinolin-6-ylbenzenesulfonamide (5)

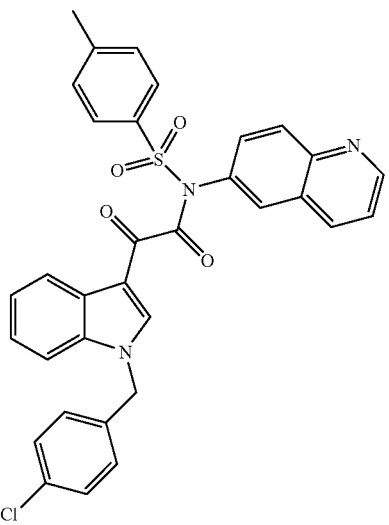

MS: m/e=594 (M+H$^+$)

Biological Data:

EXAMPLE 6

Inhibition of selected tumor cell lines:

Substance 1 was investigated for its antiproliferative action in a proliferation test using established tumor cell (D. A. Scuderio et al. Cancer Res. 1988, 48, 4827–4833). The test used determines the cellular dehydrogenase activity and permits a determination of the cell vitality and, indirectly, of the cell count. The cell lines used are the human cervical carcinoma cell line KB/HeLa (ATCC CCL17), the ovarial adeno carcinoma cell line SKOV-3 (ATCC HTB77), the human glioblastoma cell line SF-268 (NCl 503138) and the pulmonary carcinoma cell line NCl-H460 (NCl 503473).

TABLE 1

Proliferation inhibition of the present invention's ssubstances in XTT cytotoxicity test on human tumor cell lines

| Compound | KB/HeLa IC50 [µg/ml] | NCI-H460 IC50 [µg/ml] | SF-268 IC50 [µg/ml] | SK-OV-3 IC50 [µg/ml] |
|---|---|---|---|---|
| 1 | 0.170 | 0.222 | 0.261 | 0.139 |

EXAMPLE 7

Antiproliferative action on MDR tumor cell lines:

Substance 1 was further characterized by testing with regard to multidrug-resistant cell lines as compared with the nonresistant wild-type cell lines.

The cell lines tested are the murine cell line L1210, the acute myeloid leukemia cell line LT12 and the resistant lines L1210/mdr and LT12/mdr. Further test systems used are the murine P388 cell line (methylcholanthrene-induced lymphoid neoplasm) and the doxorubicin-resistant P388 cell line.

Table 2 summarises the results:

TABLE 2

Inhibitory effect of substance (1) in XTT proliferation test on human tumor cell lines.

| Compound | LT12 IC50 [µg/ml] | LT12mdr IC50 [µg/ml] | L1210 IC50 [µg/ml] | L1210VCR IC50 [µg/ml] | P388 IC50 [µg/ml] | P388ADR IC50 [µg/ml] |
|---|---|---|---|---|---|---|
| 1 | 0.226 | 0.277 | 0.255 | 0.577 | 0.219 | 0.252 |

We claim:
1. An N-substituted indolyl-3-glyoxylamide as in the general formula I

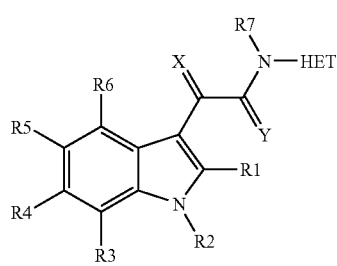

in which
R1, R3–R6:
  are hydrogen,
  unsubstituted or substituted alkyl,
  unsubstituted or substituted cycloalkyl,
  unsubstituted or substituted aryl,
  unsubstituted or substituted heteroaryl,
  unsubstituted or substituted alkylaryl,
  unsubstituted or substituted alkylheteroaryl,
  amino, monoalkylamino, dialkylamino,
  halogen, alkyl substituted by one or more fluorine atoms, preferably a trifluoromethyl group, cyano, straight-chain or branched cyanoalkyl, alkylcarbonyl, carboxyl, alkoxycarbonyl, carboxyalkyl or alkoxycarbonylalkyl, alkoxy, arylalkoxy, preferably benzyloxy, alkoxycarbonylamino, alkoxycarbonylaminoalkyl, R2:
is unsubstituted or substituted alkyl,
unsubstituted or substituted alkylaryl,
unsubstituted or substituted alkylheteroaryl, R7: is a sulfone of the formula —$SO_2$-X1, where X1 is N(alk)$_2$, hydroxyl, unsubstituted or substituted alkyl, unsubstituted or substituted cycloalkyl, unsubstituted or substituted aryl, unsubstituted or substituted heteroaryl, unsubstituted or substituted alkylcycloalkyl, unsubstituted or substituted alkylheterocyclyl, unsubstituted or substituted alkylaryl, unsubstituted or substituted alkylheteroaryl;

C(O)—X2, where X2 is unsubstituted or substituted aryl, unsubstituted or substituted heteroaryl, unsubstituted or substituted alkylaryl and unsubstituted or substituted alkylheteroaryl, C(O)O—X3, where X3 is unsubstituted or substituted cycloalkyl, unsubstituted or substituted heterocyclyl, unsubstituted or substituted aryl, unsubstituted or substituted heteroaryl, unsubstituted or substituted alkylcycloalkyl, unsubstituted or substituted alkylheterocyclyl, and unsubstituted or substituted alkylheteroaryl, C(O)NX4X5, where X4 and X5 independently of one another are hydrogen, unsubstituted or substituted alkyl, unsubstituted or substituted cycloalkyl, unsubstituted or substituted heterocyclyl, unsubstituted or substituted aryl, unsubstituted or substituted heteroaryl, unsubstituted or substituted alkylcycloalkyl, unsubstituted or substituted alkylheterocyclyl, unsubstituted or substituted alkylaryl, unsubstituted or substituted alkylheteroaryl, or X4 and X5 together are cycloalkyl or cycloheteroalkyl, C(S)NX6X7, where X6 and X7 independently of one another are hydrogen, unsubstituted or substituted alkyl, unsubstituted or substituted cycloalkyl, unsubstituted or substituted heterocyclyl, unsubstituted or substituted aryl, unsubstituted or substituted heteroaryl, unsubstituted or substituted alkylcycloalkyl, unsubstituted or substituted alkylheterocyclyl, unsubstituted or substituted alkylaryl, unsubstituted or substituted alkylheteroaryl, or X6 and X7 together are cycloalkyl or cycloheteroalkyl, X: is O, S or geminally linked hydrogen and hydroxyl, Y: is O, S and HET: is one or more heteroatoms selected from the group consisting of a saturated, unsaturated or aromatic (C2–C14)-heterocycle comprising N, O and S, which can be bonded to the amide nitrogen directly or via a (C1–C6)-alkyl bridge and the alkyl radical can be substituted or unsubstituted and one or two aryl or cycloalkyl groups can be fused to the heterocycle, where the alkyl radical can in all cases be branched or unbranched and saturated or unsaturated and where the heterocycle, aryl or cycloalkyl groups can be unsubstituted or substituted, or its pharmaceutically tolerable salts.

2. An N-substituted indolyl-3-glyoxylamide of the general formula I as claimed in claim 1, wherein HET can in particular be pyrrole, furan, thiophene, pyrazole, thiazole, indole, oxazole, imidazole, isothiazole, isoxazole, 1,2,3-triazole, 1,2,4-triazole, 1,2,4,oxadiazole, 1,3,4-oxadiazole, 1,2,5-thiadiazole, 1,3,4-thiadiazole, tetrazole, pyridine, pyrimidine, pyridazine, pyrazine, benzofuran, indazole, carbazole, benzoxazole, benzimidazole, benzothiazole, benzotriazole, quinoline, isoquinoline, cinnoline, quinoxaline, quinazoline, phthalazine, pyridopyrazine, 1,2,3-triazine, 1,2,4-triazine, 1,3,5-triazine, purine, pteridine, acridine and phenanthridine.

3. An N-substituted indolyl-3-glyoxylamide of the general formula I as claimed in claim 1, comprised by neutralization of its basic compounds with inorganic or organic acids or by neutralization of its acidic compounds with inorganic or organic bases.

4. An N-substituted indolyl-3-glyoxylamide of the general formula I as claimed in claim 1 having at least one asymmetric carbon atom in the form of its racemate, in the form of a pure enantiomer and/or diastereoisomer or in the form of a mixture of these enantiomers and/or diastereoisomers, in the form of a tautomer, its solvate or hydrate.

5. An N-substituted indolyl-3-glyoxylamide of the general formula I as claimed in claim 1, which is one of the compounds:

N-{2-[1-(4-chlorobenzyl)-1H-indol-3-yl]-2-oxoacetyl}-N-quinolin-6-yl-benzamide (1)

N-{2-[1-(4-chlorobenzyl)-1H-indol-3-yl]-2-oxoacetyl}-2-phenyl-N-quinolin-6-yl-acetamide (2)

phenyl{2-[1-(4-chlorobenzyl)-1H-indol-3-yl]-2-oxoacetyl}quinolin-6-ylcarbamate (3)

(1R,2S,5R)-2-isopropyl-5-methylcyclohexyl{2-[1-(4-chlorobenzyl)-1H-indol-3-yl]-2-oxoacetyl}quinolin-6-ylcarbamate (4)

N-{2-[1-(4-chlorobenzyl)-1H-indol-3-yl]-2-oxoacetyl}-4-methyl-N-quinolin-6-yl-benzenesulfonamide (5).

6. A pharmaceutical composition comprising an N-substituted indolyl-3-glyoxylamide of the general formula I as claimed in claim 1 and a pharmaceutically acceptable carrier.

7. A method for the treatment of tumors in a mammal, which comprises administering an N-substituted indolyl-3-glyoxylamide of the general formula I as claimed in claim 1 to the mammal.

8. A process for the preparation of the N-substituted indolyl-3-glyoxylamides of the general formula I as claimed in claim 1, comprising reactions according to the following scheme:

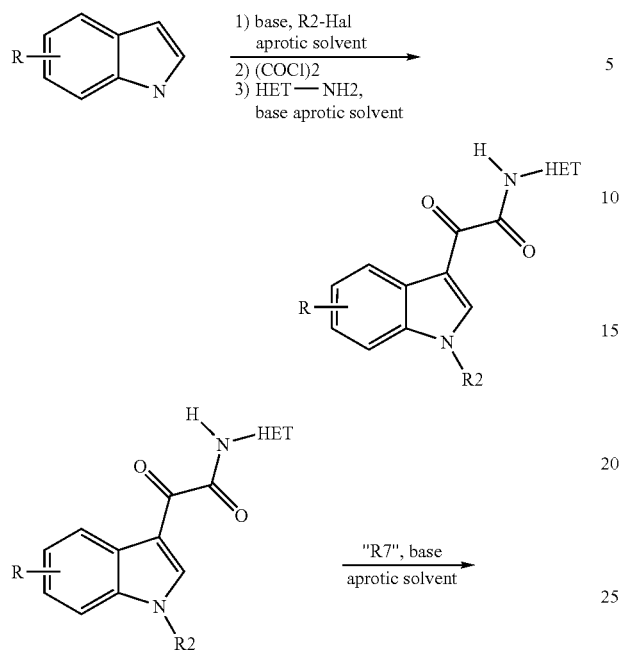

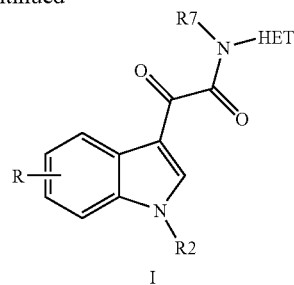

9. A composition comprising at least one N-substituted indolyl-3-glyoxylamide of the general formula I as claimed in claim 1.

10. The composition as claimed in claim 9, further comprising a pharmaceutically tolerable excipient, additive or vehicle.

11. A method for the treatment of benign and malignant tumors in a mammal, which comprises administering at least one N-substituted indolyl-3-glyoxylamide of the general formula I as claimed in claim 1 to the mammal in a dose which is effective for tumor treatment.

12. The method as claimed in claim 11, wherein the mammal is a human.

\* \* \* \* \*